United States Patent
Okuda et al.

(10) Patent No.: US 6,291,655 B1
(45) Date of Patent: Sep. 18, 2001

(54) BINUCLEAR METAL HYDRIDE COMPLEXES AS CATALYSTS FOR THE (CO)POLYMERIZATION OF POLAR MONOMERS

(75) Inventors: Jun Okuda, Ingelheim; Kai Hultzsch, Wiesbaden; Michael Geprägs, Lambsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/372,813

(22) Filed: Aug. 12, 1999

(30) Foreign Application Priority Data

Aug. 14, 1998 (DE) ............................... 198 36 819

(51) Int. Cl.[7] ............... C07F 17/00; B01J 31/00
(52) U.S. Cl. ............ 534/15; 502/152; 502/158; 502/155; 526/160; 526/943; 534/11
(58) Field of Search ............ 556/1; 534/11, 534/15; 502/152, 155, 158; 526/160, 943

(56) References Cited

U.S. PATENT DOCUMENTS

| 5,312,881 | 5/1994 | Marks et al. ............ 526/126 |
| 5,464,906 | 11/1995 | Patton et al. ............ 525/240 |

FOREIGN PATENT DOCUMENTS

| 634 429 | 1/1995 | (EP) . |

OTHER PUBLICATIONS

Shapiro et al., "Unique Example of a Single–Composition α–Olefin Polymerization Catalyst" Organometallics vol. 9 (1990) pp. 867–869.

Shapiro et al. "Model Ziegler–Natta α–Olefin Polymerization Catalysts Derived from [{($\eta^5$-$C_5Me_4$)$SiMe_2$($\eta^1$-$NCMe_3$)}($PMe_3$)$Sc(\mu_2$-H)]$_2$ and [{($\eta^5$-$C_5Me_4$)$SiMe_2$($\eta^1$-$NCMe_3$)}$Sc(\mu_2$-$CH_2CH_2CH_3$)]$_2$. Synthesis, Strucutres, and Kinetic and Equilibrium Investigations of the Catalytically Active Species in Solution" J. Am. Chem. Soc. vol. 116 (1994) pp. 4623–4640.

Mu et al. "Use of Alkane Elimination in the One–Step Synthesis of Organoscandium Complexes Containing a New Multidentate Cyclopentadienyl Ligand" Organometallics vol. 15, (1996) pp. 2720–2726.

Bull.Chem. Soc. Jpn. 70, 1745–1767 (1997).

J. Am. Chem. Soc. 1984, 106, 1291–1300.
Org. 1997, 16, 3511–3522.
Eur. Plym. J. vol. 33, No. 4, 577–578 (1997).
Macromolecules 1992, 25, 5115–5116.
Chineses Jr. of Appl. Chem, vol. 12, No. 3, 1995.
Org. 1996, 15, 2720–2726.
Org. 1994, 13, 69–82.

*Primary Examiner*—Porfirio Nazario-Gonzalez
(74) *Attorney, Agent, or Firm*—Keil & Weinkauf

(57) ABSTRACT

In binuclear metal hydride complexes of the formuula (I)

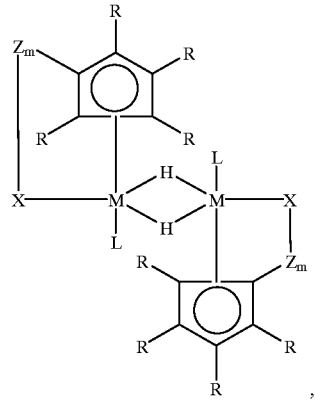

the substituents and indices have the following meanings:
M is scandium, yttrium, lanthanum or a lanthanide metal,
R is hydrogen, halogen, $C_1$–$C_{20}$-alkyl, $C_3$–$C_1$-cycloalkyl, $C_6$–$C_{15}$-aryl or $C_3$–$C_{30}$-organosilyl, where two adjacent radicals R can also form a saturated or unsaturated, cyclic or heterocyclic group having from 4 to 18 carbon atoms,
Z is —$SiR'_2$—, —$CR'_2$—, —$GeR'_2$—, —$SnR'_2$—, —BR'— or —O—,
R' is $C_1$–$C_{20}$-alkyl, $C_3$–$C_{10}$-cycloalkyl, $C_6$–$C_{15}$-aryl or alkylaryl having from 1 to 10 carbon atoms in the alkyl part and from 6 to 10 carbon atoms in the aryl part,
m is 1 or 2,
X is —O—, —S—, —NR"—, —PR"—, —OR", —SR", —$NR"_2$ or —$PR"_2$,
R" is hydrogen, $C_1$–$C_{20}$-alkyl, $C_3$–$C_{10}$-cycloalkyl, $C_6$–$C_{15}$-aryl, alkylaryl having from 1 to 10 carbon atoms in the alkyl part and from 6 to 10 carbon atoms in the aryl part or $C_3$–$C_{30}$-organosilyl and L is a low molecular weight, Lewis-basic, organic compound.

2 Claims, No Drawings

BINUCLEAR METAL HYDRIDE COMPLEXES AS CATALYSTS FOR THE (CO)POLYMERIZATION OF POLAR MONOMERS

The present invention relates to binuclear metal hydride complexes of the formula (I)

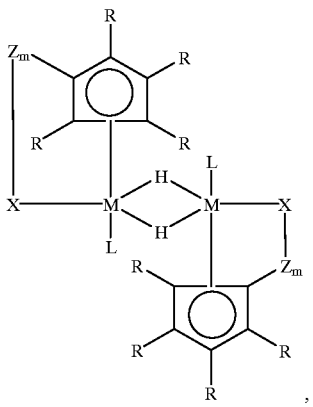

where the substituents and indices have the following meanings:

M is scandium, yttrium, lanthanum or a lanthanide metal,
R is hydrogen, halogen, $C_1$–$C_{20}$-alkyl, $C_3$–$C_{10}$-cycloalkyl, $C_6$–$C_{15}$-aryl or $C_3$–$C_{30}$-organosilyl, where two adjacent radicals R can also form a saturated or unsaturated, cyclic or heterocyclic group having from 4 to 18 carbon atoms,
z is —SiR'$_2$—, —CR'$_2$—, —GeR'$_2$—, —SnR'$_2$—, —BR'— or —O—,
R' is $C_1$–$C_{20}$-alkyl, $C_3$–$C_{10}$-cycloalkyl, $C_6$–$C_{15}$-aryl or alkylaryl having from 1 to 10 carbon atoms in the alkyl part and from 6 to 10 carbon atoms in the aryl part,
m is 1 or 2,
X is —O—, —S—, —NR"—, —PR"—, —OR", —SR", —NR"$_2$ or —PR"$_2$,
R" is hydrogen, $C_1$–$C_{20}$-alkyl, $C_3$–$C_{10}$-cycloalkyl, $C_6$–$C_{15}$-aryl, alkylaryl having from 1 to 10 carbon atoms in the alkyl part and from 6 to 10 carbon atoms in the aryl part or $C_3$–$C_{30}$-organosilyl and
L is a low molecular weight, Lewis-basic, organic compound.

The invention also provides a process for preparing said binuclear metal hydride complexes and provides for their use as catalysts for the (co)polymerization of polar monomers. In addition, the invention relates to a process for preparing (co)polymers from polar monomers.

In recent times, complexes based on rare earth metals have been increasingly examined for suitability as catalysts for the coordinatively controlled polymerization of both nonpolar and polar, olefinically unsaturated monomers (cf. H. Yasuda, E. Ihara, Bull. Chem. Soc. Jpn. 1997, 70, pp. 1745–1767). Polar monomers such as acrylates or acrylonitrile have, however, hitherto still been polymerized by free-radical methods, particularly in industrial processes. However, free-radical polymerization processes are frequently difficult to control and lead to polymer products having a broad molecular weight distribution. First indications are that selected catalysts based on rare earth metals can also be polymerization-active for polar monomers.

For example, Jiang et al., Eur. Polym. J., 1997, 33 (4), pp. 577–578, use multicomponent catalyst systems based on lanthanides substituted by 2-ethylhexyl phosphonate for the polymerization of acrylonitrile. Further necessary catalyst constituents are dibutylmagnesium and N,N,N',N'-tetramethyl-ethylenediamine, in each case in excess based on the rare earth metal. To obtain an active catalyst species, the catalyst mixture has to be additionally subjected to an aging process. The monomer conversion achieved is generally not above 50%.

Similarly to the case of metallocene compounds based on the early transition metals, it is possible to prepare polymerization-active sandwich complexes of the rare earth metals. U.S. Pat. No. 5,312,881 describes bridged mononuclear biscyclopentadienyl complexes of the lanthanides by means of which α-substituted acrylates can be copolymerized. A Lewis-acid cocatalyst such as methylaluminoxane may have to be added to the catalyst system to obtain a satisfactory polymerization result. In EP-A 0 634 429, it is stated that block copolymers can be obtained from polar and nonpolar monomers with the aid of bridged mononuclear sandwich complexes of samarium (cf. Yasuda et al., Macromolecules, 1992, 25, pp. 5115–5116). However, the metallocene complex to be used is extremely sensitive or unstable and can essentially not be analyzed spectroscopically. Accordingly, the preparation of bridged sandwich complexes is generally more complicated than the preparation of sandwich or semisandwich complexes.

U.S. Pat. No. 5,464,906 describes binuclear, amidobridged cyclopentadienyl complexes based on metals of transition group III of the Periodic Table of the Elements. These complexes are suitable for the homopolymerization of α-olefins, in particularly ethene. The polymerization of polar monomers is not discussed.

The binuclear rare earth metal complex [SmH($C_5Me_5$)$_2$]$_2$ allows, as Yasuda et al., Bull. Chem. Soc. Jpn., 1997, 70 (8), pp. 1745–1767, were able to show, the polymerization of polar monomers. However, only alkyl methacrylates can be polymerized using this catalyst, albeit in high yield and over a relatively wide temperature range. The binuclear metal complex [Y(OMe)($C_5Me_5$)$_2$]$_2$ again displays no polymerization activity in respect of polar monomers. In contrast, Ren et al., Chin. J. Appl. Chem., 1995, 12, p. 105, were able to polymerize acrylonitrile in small yields using binuclear neodymium complexes of the type [NdMe(t-BuCp)$_2$]$_2$ (t-Bu=tert-butyl, Cp=cyclopentadienyl).

Mu et al., Organometallics, 1996, 15, pp. 2720–2726, synthesized binuclear scandium hydride semisandwich complexes using a multidentate cyclopentadienyl ligand and used the complexes obtained for the polymerization of nonpolar olefins such as 1-hexene. However, no reaction at all was found at room temperature while at elevated temperatures small amounts of a rubber-like product which was not analyzed further were obtained. The polymerization of polar monomers is not discussed at any point in Mu et al.

Schaverien, Organometallics, 1994, 13 (1), pp. 69–82, were able to prepare the binuclear yttrium hydride semisandwich complex [Y($C_5Me_5$)(OAr)($\mu$-H)]$_2$ (Ar=–2,6-$C_6H_3$-(t-Bu)$_2$), but this is obtained only in a moderate yield. Longer reaction times (>3h) lead to formation of a by-product in not inconsiderate amounts. The binuclear yttrium hydride semisandwich complex obtained proved to be moderately polymerization-active toward nonpolar olefinically unsaturated monomers. The polymerization of polar monomers was not studied.

According to Duchateau et al., Organometallics, 1997, 16, pp. 3511–3522, the binuclear yttrium hydride complex {[(O-t-Bu)Me$_2$Si(N-t-Bu)]$_2$Y($\mu$-H)}$_2$ obtained from [(O-t-Bu)Me$_2$Si(N-t-Bu)]Y[CH(SiMe$_3$)$_2$] by hydrogenation can, owing to insufficient stability, be detected only by $^1$H-NMR spectroscopy but cannot be isolated. It is not suitable as a catalyst for the polymerization of nonpolar or polar monomers. Furthermore, in the case of the binuclear yttrium hydride complex of the formula $[(C_5H_4R)_2Y(\mu\text{-H})(THF)]_2$ (R=H or Me), insertion was observed in the presence of acetonitrile as polar monomer to give the corresponding imido complex, but polymerization to polyacrylonitrile was not observed (cf. Evans et al., J. Am. Chem. Soc., 1984, 106, p. 1291).

It would therefore be desirable to find stable complexes of the rare earth metals which are suitable for the polymerization of a broad range of polar monomers and at the same time can be obtained simply, unproblematically and inexpensively.

It is an object of the present invention to find stable, readily obtainable metal complexes of the rare earth metals by means of which a variety of monomers can be coordinatively polymerized in a satisfactory manner.

We have found that this object is achieved by the binuclear metal hydride complexes described at the outset. We have also found a process for preparing said binuclear metal hydride complexes, which are suitable, for example, as catalysts for the (co)polymerization of polar monomers. In addition, a process for preparing (co)polymers from polar monomers has been found.

Preferred binuclear metal hydride complexes are compounds of the formula (I) in which
M is yttrium,
R is $C_1$–$C_{10}$-alkyl or $C_3$–$C_{21}$--organosilyl, where two adjacent radicals R can also form a fused aromatic ring,
Z is —SiR'$_2$— or —CR'$_2$—,
R' is $C_1$–$C_{10}$-alkyl or $C_6$–$C_{10}$-aryl,
m is 1,
X is —NR"— or —PR"—,
R" is $C_1$–$C_{10}$-alkyl, $C_6$–$C_{10}$-aryl or alkylaryl having from 1 to 6 carbon atoms in the alkyl part and from 6 to 10 atoms in the aryl part and
L is tetrahydrofuran, 2,5-dialkyltetrahydrofuran, dioxane, dialkyl ether, acetonitrile, triarylphosphine or halogenated triarylphosphine.

In the binuclear complexes (I) of the present invention, the central metal M is one of the rare earth metals, i.e. scandium, yttrium, lanthanum or a lanthanide metal, i.e. cerium, praseodymium, neodymium, promethium, samarium, europium, gadolinium, terbium, dysprosium, holmium, erbium, thulium, ytterbium and lutetium (cf. Lehrbuch der anorganischen Chemie, Holleman-Wiberg, de Gruyter, Berlin, 1985, p. 59). Preference is given to yttrium, lanthanum, lutetium, erbium and ytterbium; particular preference is given to yttrium. The metals M are generally present in the mononuclear complexes in formally triply positively charged form.

The monoanionic, $\eta^5$-bonded, cyclic ligand bearing the substituent -(Z$_m$)- can be cyclopentadienyl (R=H) or a singly negatively charged five-membered carbocycle which is substituted by, apart from the radical Z, one or more radicals R, for example by halogen such as fluorine, chlorine or bromine, linear or branched $C_1$–$C_{20}$-alkyl, preferably $C_1$–$C_{10}$-alkyl such as methyl, ethyl, n-propyl, i-propyl, n-butyl or t-butyl, $C_3$–$C_{10}$-cycloalkyl, preferably $C_3$–$C_7$-cycloalkyl such as cyclopropyl or cyclohexyl, or $C_6$–$C_{15}$-aryl, preferably $C_6$–$C_{10}$-aryl such as phenyl or naphthyl. Suitable aryl substituents include, for example, $C_6$–$C_{15}$-aryl, preferably $C_6$–$C_{10}$-aryl, substituted by $C_1$–$C_6$-alkyl such as methyl or i-propyl or by halogen such as fluorine, chlorine or bromine. Two adjacent radicals R can also together form a saturated or unsaturated, cyclic or heterocyclic group having from 4 to 18, preferably from 4 to 15, carbon atoms. Examples of such groups are fused-on aryl units. Accordingly, indenyl, fluorenyl or benzindenyl systems are likewise suitable monoanionic $\eta^5$-bonded cyclic ligands.

Further suitable radicals R are $C_3$–$C_{30}$—, preferably $C_3$–$C_{21}$-organosilyl groups, —Si(R*)$_3$. The radicals R* can be, independently of one another, $C_1$–$C_{10}$-alkyl, preferably $C_1$–$C_7$-alkyl, e.g. methyl, ethyl or i-propyl, $C_3$–$C_{10}$-cycloalkyl, preferably $C_3$–$C_7$-cycloalkyl, e.g. cyclopropyl or cyclohexyl, $C_6$–$C_{10}$-aryl, preferably phenyl, or alkylaryl having from 1 to 4 carbon atoms in the alkyl part and from 6 to 10 carbon atoms in the aryl part, for example benzyl.

In a compound (I), the radicals R can be either identical or different. Among the abovementioned compounds, particularly suitable $\eta^5$-bonded ligands complexing the metal M are ones derived from cyclopentadienyl, tetra-$C_1$–$C_6$-alkylcyclopentadienyl, indenyl, fluorenyl or benzindenyl, where the last three ligands mentioned can also be substituted by one or more $C_1$–$C_6$-alkyl groups. Preferred radicals bearing the substituent Z are cyclopentadienyl, tetra-$C_1$–$C_4$-alkylcyclopentadienyl, indenyl, benzindenyl and indenyl or benzindenyl substituted by from 1 to 3 $C_1$–$C_4$-alkyl groups. Particular preference is given to using Z-substituted cyclopentadienyl, tetramethylcyclopentadienyl or indenyl, in particular tetramethylcyclopentadienyl. It is usual to use binuclear complexes (I) which have two identical $\eta^5$-bonded ligands. However, these ligands can also differ from one another in their ring system as such and/or in their ring substitution pattern.

Suitable radicals Z are bivalent structural units based on single-atom bridges whose free valencies may be satisfied by organic radicals R'. Examples of suitable bridges are the silyl (—SiR'$_2$—), alkyl- (—CR'$_2$—), germanyl (—GeR'$_2$—), stannyl (—SnR'$_2$—), boranyl (—BR'—) and oxo (—O—) groups. It is also possible for two units Z covalently bound to one another (m=2) to form a bridging segment between the inonoanionic, $\eta^5$-bonded ligand and the unit X. In such a bridging segment, Z naturally does not necessarily have to be present in the form of two identical structural units. Suitable two-membered bridging segments are, in particular, the systems —SiR'$_2$—SiR'$_2$—, —SiR'$_2$—CR'$_2$—, —CR'$_2$—CR'$_2$—, —CR'=CR'—, —O—CR'$_2$— and —O—SiF'$_2$—. However, preference is given to using bridging segments containing a single bridging atom (m=1), in particular the systems —SiR'$_2$— and —CR'$_2$—. The radicals R' can be $C_1$–$C_{20}$-alkyl, preferably $C_1$–$C_{10}$-alkyl, for example methyl, ethyl or i-propyl, $C_3$–$C_{10}$-cycloalkyl, preferably $C_3$–$C_7$-cycloalkyl, for example cyclohexyl, $C_6$–$C_{15}$-aryl, preferably $C_6$–$C_{10}$-aryl, in particular phenyl, or alkylaryl having from 1 to 10 carbon atoms in the alkyl part and from 6 to 10 carbon atoms in the aryl part, for example benzyl. Particularly preferred radicals Z are di-$C_1$–$C_7$-alkyl-substituted silyl groups such as dimethylsilyl, diethylsilyl or di-i-propylsilyl.

Examples of units X include the oxo (—O—), thio (—S—), amido (—NR'—) and phosphido (—PR"—) groups. These groups are generally bound to the metal center M via a $\eta^1$ bond. X can also be a neutral two-electron donor such as —OR", —SR", —NR"$_2$ or —PR"$_2$. The latter radicals X are usually coordinatively bound to the metal center M via a free electron pair. X is preferably an oxo or thio group, particularly preferably an amido unit. As substituent R" in the radicals —NR"—, —PR"—, —OR", —SR", —NR$_2$ or —PR"$_2$ use is generally made of hydrogen, $C_1$–$C_{20}$-alkyl, $C_3$–$C_{10}$-cycloalkyl, $C_6$–$C_{15}$-aryl, alkylaryl having from 1 to 10 carbon atoms in the alkyl part and from 6 to 10 carbon atoms in the aryl part or $C_3$–$C_{30}$- organosilyl. Particularly useful radicals R" are bulky groups such as $C_3$–$C_{10}$-alkyl groups, for example i-propyl or t-butyl, $C_6$–$C_{10}$-aryl groups such as phenyl or substituted phenyl and alkylaryl groups having from 1 to 6 carbon atoms in the alkyl part and from 6 to 10 carbon atoms in the aryl part, for example benzyl. -N(t-butyl)- is particularly frequently used as the unit X.

Suitable ligands L which are coordinatively bound to the metal center are low molecular weight organic Lewis bases in general, i.e. compounds which have a two-electron donor function. Examples of ligands L are tetrahydrofuran, 2,5-dialkyltetrahydrofuran such as 2,5-dimethyltetrahydrofuran, dioxane, dialkyl ethers such as dimethyl ether or diethyl ether, acetonitrile, triarylphosphine, in particular triethylphosphine, or partially halogenated or perhalogenated triarylphosphine such as tris(p-fluorophenyl)-phosphine or tris(pentafluorphenyl)phosphine. L is preferably tetrahydrofuran.

In the binuclear metal complex (I) of the present invention, the ligands and radicals which occur twice, viz. R, R', R", Z, X, and L, and the central metal M and the $\eta^5$-bonded ligand system can each be identical or different in a single compound (I). In general, the ligands, the radicals and the central metals M are in each case identical.

Particularly preferred binuclear metal hydride complexes are, for example,
bis[tetramethylcyclopentadienyl(tert-butylamido) dimethylsilyl-yttrium hydride], bis[tetramethylcyclopentadienyl(benzylamido)-dimethylsilylyttrium hydride], bis[indenyl(tert-butylamido) dimethylsilylyttrium hydride] or bis[indenyl(benzylamido) dimethylsilylyttrium hydride].

The binuclear complexes of the present invention having the formula(I) are obtained by hydrogenation of mononuclear metal complexes of the formula (II)

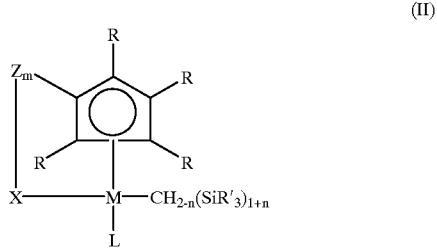

(II)

where n=0 or 1 and the other substituents and indices have the general or preferred meanings which have already been indicated above.

The preparation of the binuclear complexes (I) is usually carried out in the presence of hydrogen under a pressure in the range from 1.5 to 100 bar, preferably in the range from 2 to 20 bar, and at a temperature in the range from 0 to 1000C, preferably from 10 to 80° C. At reaction times in the range from 2 to 24 hours, but even at less than 10 hours, the metal complex of the present invention is usually obtained in high yield, possibly in the form of an isomer mixture. In general, the preparation of the binuclear complex (I) is carried out in an inert solvent, for example a low molecular weight aliphatic hydrocarbon such as n-pentane, n-hexane or cyclohexane, an aromatic hydrocarbon such as benzene, toluene or xylene or a halogenated hydrocarbon such as dichloromethane or chloroform. Preference is given to using aliphatic hydrocarbons such as n-pentane and n-hexane. Complexes of the formula (I) are very thermally stable and, even at 50° C., undergo no CH activation or El/D exchange with deuterated solvents. Mononuclear complexes of the formula (II) can be obtained unproblematically, for example starting from compounds of the type $Y[CH_{2-n}(SiMe_3)_{1+n}]_3$ (III) by reaction with compounds such as $[C_5R_4(H)(SiR'_2\text{-}XH)]$ (IV), e.g. $[C_5Me_4(H)(SiMe_2NHt\text{-}Bu)]$. At a reaction temperature in the range from −20 to 50° C., reaction times of from 1 to 5 hours are usually sufficient to achieve quantitative yields in aliphatic solvents such as n-hexane.

The metal complex (I) defined according to the present invention can be used either as such or in the form of any mixture of compounds having the formula (I) as catalyst for the polymerization of polar monomers, in particular polar olefinically unsaturated monomers, and for the polymerization of lactones.

Polar olefinically unsaturated monomers include vinyl cyanides such as acrylonitrile or methacrylonitrile, acrylic acid and the $C_1$–$C_{20}$-alkyl- and $C_6$–$C_{15}$-arylesters of acrylic acid, likewise methacrylic acid and the $C_1$–$C_{20}$-alkyl and $C_6$–$C_{15}$-aryl esters of methacrylic acid, or mixtures thereof and also lactones, in particular those containing from 3 to 10 ring carbons. It is also possible to use any mixtures of lactones. Suitable acrylates are, in particular, methyl, ethyl, propyl, n-butyl, t-butyl, 2-ethylhexyl, glycidyl and phenyl acrylate; suitable methacrylates are methyl, ethyl, propyl, n-butyl, t-butyl, 2-ethylhexyl, glycidyl and phenyl methacrylate. Among the lactones, particular mention may be made of propyllactone, valerolactone and caprolactone. Particularly preferred polar monomers are n-butyl, t-butyl, 2-ethylhexyl and glycidyl acrylate and also acrylonitrile and mixtures thereof.

The polymerization of the polar monomers in the presence of compounds (I) can be carried out in bulk or in solution. If polymerization is carried out in solution, preference is given using aprotic solvents. For example, it is possible to use aliphatic hydrocarbons such as pentane or hexane, aromatic hydrocarbons such as benzene, toluene or xylene, or halogenated hydrocarbons such as dichloromethane or chloroform. Low molecular weight linear or cyclic ether compounds such as diethyl ether or tetrahydrofuran can also be used. Preference is given to using aromatic hydrocarbons, in particular toluene. The starting concentration of the monomers is generally set to a value in the range from 0.001 to 5 mol/l, preferably from 0.01 to 4 mol/l. The polymerization temperature can be varied over a wide range. It is usual to select a temperature in the range from −70 to 90° C., preferably from 10 to 60° C. The polymerization time is generally within the range from 1 to 50 hours; reaction times of from 3 to 24 hours have been found to be useful. The polymerization reactions are successful at atmospheric pressure and also at pressures in the range from 0.001 to 50 bar. The polymerization is usually carried out at pressures in the range from 0.5 to 10 bar.

The polymerization reactions described are preferably carried out under inert reaction conditions, i.e. with exclusion of oxygen and moisture. If appropriate, a protective gas such as argon or nitrogen can also be employed.

To initiate the polymerization, it has been found to be advantageous to add the complex (I) of the present invention to the monomer solution, but it is naturally also possible for the complex (I) to be initially charged as such or in dissolved form. The polymerization usually does not require the addition of further coactivators or cocatalysts. The ratio of monomer to catalyst is usually from 100 to 10,000, preferably from 100 to 5000.

The polymers obtained in the presence of binuclear metal hydride complexes (I) of the present invention are usually obtained in atactic form. It is possible to achieve molecular weights $M_n$ in the range from 5000 to 500,000 and also preferably greater than 10,000 g/mol. The polydispersities ($M_w/M_n$) achieved are generally less than 2.0, but can readily take on values of less than 1.70.

Naturally, the binuclear metal hydride complexes described provide not only a route to, for example, homopolyacrylonitrile or homopolyacrylates, but also to block copolymers. Examples which may be mentioned are poly(acrylonitrile-b-ethyl acrylate), poly(tert-butyl acrylate-b-methyl acrylate), poly(acrylonitrile-b-ε-caprolactone) and poly(tert-butylacrylate-b-ε-caprolactone). The block copolymers mentioned are advantageously synthesized by sequential addition of the individual components. The next block monomer material is generally added only when the previously added monomer has reacted completely.

The polymerization reaction is generally stopped by addition of an aprotic compound, for example a low molecular weight alcohol such as methanol, ethanol or i-propanol. The (co)polymer obtained generally precipitates as a solid and can be separated off mechanically, e.g. by means of filtration. The (co)polymers obtained by the process described are suitable for the production of fibers, films and moldings.

The homopolymeric and copolymeric acrylates obtained according to the process described can be used, inter alia, as impact modifiers in thermoplastic polymers or polymer blends. As suitable thermoplastic polymers or blend components, mention may be made of polyamides and polyesters. Polyacrylonitrile is suitable, inter alia, as a fiber material.

The binuclear metal hydride complexes of the present invention are simple and economical to prepare and have good thermal stability. They are suitable for the polymerization of a broad range of polar monomers, for example acrylates and also vinyl cyanides. It is also possible to polymerize lactones. The abovementioned process enables homopolymers, copolymers and block copolymers to be obtained. Furthermore, the polymers obtained have a low polydispersity. Since addition of cocatalysts or coactivators is not necessary, the polymers are obtained directly, i.e. without additional purification steps, in very high purity.

The present invention is illustrated by the examples below.

EXAMPLES

The molecular weights of the homopolymers prepared were determined by end group analysis using quantitative $^1$H-NMR spectroscopy.

The $^1$H-NMR-, $^{13}$C-NMR- and $^{29}$Si-NMR-spectroscopic measurements were carried out on a Bruker DRX 400 instrument.

I) Preparation of a binuclear yttrium hydride complex a) Preparation of $Y(CH_2SiMe_3)_3(THF)_2$ Yttrium chloride (586 mg) was taken up in tetrahydrofuran (THF) (30 ml) and stirred at 55° C. for 30 minutes. The solvent was removed by distillation and the solid residue was admixed with hexane (40 ml) and THF (0.3 ml). At −780° C., a solution of $LiCH_2SiMe_3$ (856 mg) in hexane (20 ml) was added and the suspension obtained was stirred at 0° C. for 1.5 hours. Filtration of the reaction mixture gave $Y(CH_2SiMe_3)_3(THF)_2$ in the form of colorless microcrystals. $^1$H-NMR($C_6D_6$, 25° C.): δ=−0.71 (d, $^2$J(Y,H)=2.3 Hz, 6H; Y—$CH_2$), 0.27 (s, 27 H; $SiCH_3$), 1.30 (m, 8 H; β-$CH_2$), 3.93 (m, 8 H; α-$CH_2$); $^{13}$C-NMR ($C_6D_6$, 25° C.): δ=4.6 ($SiCH_3$), 25.0 (β-$CH_2$), 33.7 (d, $^1$J(Y,C)=35.7 Hz, Y—$CH_2$), 70.8 (β-$CH_2$).

b) Preparation of $[(N-t-Bu)(SiMe_2)(C_5Me_4)]Y(CH_2SiMe_3)$ (THF)

A solution $[C_5Me_4(H)(SiME_2NHt-Bu)]$ (186 mg) in hexane (5 ml) was added at 0° C. to $Y(CH_2SiMe_3)_3(THF)_2$ (365 mg) in pentane (10 ml) and the mixture was stirred for 2 hours at this temperature. The decanted reaction solution was evaporated under reduced pressure and the desired product was obtained by means of crystallization in cold pentane (−30° C.) in the form of colorless microcrystals (320 mg). ($[C_5Me_4(H) (SiMe_2NHt-Bu)]$ was prepared by a method of Shapiro et al., J. Am. Chem. Soc. 1994, 116, p. 4623.) $^1$H-NMR: δ=−0.93 (d, $^2$J(Y,H)=3.1 Hz, 2H; Y—$CH_2$), 0.28 (s, 9 H, $CH_2SiCH_3$), 0.74 (s, 6 H, $SiCH_3$), 1.08 (br s, 4 H, β-$CH_2$), 1.38 (s, 9 H, $C(CH_3)_3$), 2.04, 2.19 (s, 6 H, $C_5Me_4$), 3.36 (br s, 4 H, α-$CH_2$); $^{13}$C-NMR δ=4.7 ($CH_2SiCH_3$), 8.4 ($NSiCH_3$), 11.5, 14.0 ($C_5Me_4$), 24.7 (β-$CH_2$), 26.2 (d, $^1$J(Y,C)=44.9 Hz, Y—$CH_2$), 36.0 ($C(CH_3)_3$), 54.0 ($C(CH_3)_3$), 70.7 α-$CH_2$), 106.6 ($C_5Me_4$ C—$SiCH_3$), 122.3, 126.4 ($C_5Me_4$), $^{29}$Si—NMR: δ=−25.0 ($NSiMe_2$), −2.7 (d, $^2$J(Y,Si)=1.9 Hz, $CH_2SiMe_3$).

c) Preparation of $\{[(N-t-Bu)(SiMe_2)(C_5Me_4)]Y(\mu-H)(THF)\}_2$

A solution of $[(N-t-Bu)(SiMe_2)(C_5Me_4)]Y(CH_2SiMe_3)$ (THF) (630 mg) in pentane (10 ml) was stirred under a hydrogen pressure of 4 bar for 7 hours at room temperature. The binuclear yttrium hydride complex was obtained as a white solid in a yield of 64%. $^1$H-NMR ($[D_8]$toluene, 50° C.): δ=0.69 (s, 6 H, $SiCH_3$), 1.36 (s, 9 H, $C(CH_3)_3$), 1.46 (br m, 4 H, β-$CH_2$), 2.09, 2.22 (s, 6 H, $C_5Me_4$), 3.82 (br m, 4 H, α-$CH_2$), 5.50 (t, 1 H, $^1$J(Y,H)=28.8 Hz, YHY); $^{13}$C-NMR ($[D_8]$toluene, 50° C.): δ=8.6 ($SiCH_3$), 12.2, 14.3 ($C_5Me_4$), 25.2 (β-$CH_2$), 36.8 ($C(CH_3)_3$), 55.0 ($C(CH_3)_3$, 72.1 (α-$CH_2$), 108.5 ($C_5Me_4C$—$SiCH_3$), 125.8 ($C_5Me_4$); $^{29}$Si—NMR: δ=−25.5.

Main isomer: $^1$H-NMR ($[D_8]$toluene, −40° C.): δ=0.81, 0.95 (s, 3 H, $SiCH_3$), 1.17 (m, 4 H, β-$CH_2$), 1.52 (s, 9 H, $C(CH_3)_3$, 2.02 (s, 6 H, $C_5Me_4$), 2.11, 2.54 (s, 3 H, $C_5Me_4$), 3.47, 3.85 (br m, 2 H, α-$CH_2$), 5.27 (t, 1H, $^1$J(Y,H)=29.0 Hz, YHY);

$^{13}$C-NMR ($[D_8]$toluene, −40° C.): δ=8.2, 9.3 ($SiCH_3$), 12.1, 12.3, 13.9, 14.7 ($C_5Me_4$), 25.0 (β-$CH_2$), 36.3 ($C(CH_3)_3$, 54.7 ($C(CH_3)_3$), 72.7 (α-$CH_2$), 107.1 ($C_5Me_4$ C—$SiCH_3$), 119.6, 122.8, 126.0, 126.2 ($C_5Me_4$); $^{29}$Si—NMR: δ=−25.6.

Secondary isomer: $^1$H-NMR ($[D_8]$toluene, −40° C.): δ=1.20, (m, 4 H, β-$CH_2$), 1.44 (s, 9 H, $C(CH_3)_3$, 2.05, 2.14, 2.20, 2.51 (s, 3 H, $C_5Me_4$), 3.78 (br m, 4 H, α-$CH_2$), 5.45 (t, 1H, $^1$J(Y,H)=28.6 Hz, YHY); $^{13}$C-NMR ($[D_8]$toluene, −40° C.): δ=8.5, 9.0 ($SiCH_3$), 11.2, 11.6, 11.8, 12.4, 13.3, 14.1, 15.2, 15.6 ($C_5Me_4$), 24.9 (β-$CH_2$), 36.4 ($C(CH_3)_3$), 55.0 ($C(CH_3)_3$), 72.4 (α-$CH_2$), 107 ($C_5Me_4$ C—$SiCH_3$), 119.9, 123.3, 125.8 ($C_5Me_4$); $^{29}$Si—NMR: δ=−25.7.

II) Polymerization Reactions a) Homopolymerization of Acrylonitrile

The binuclear complex obtained as described in I)c) (126.1 mg), dissolved in toluene (10 ml), was added to acrylonitrile (2 g) and the mixture was stirred at room temperature for 24 hours. After addition of methanol (4 ml) to the reaction mixture, polyacrylonitrile could be isolated as a white solid (480 mg).

b) Homopolymerization of t-butyl Acrylate

The binuclear complex obtained as described in I) c) (94.5 mg), dissolved in toluene (20 ml), was added to t-butyl acrylate (5.8 g) and the mixture was stirred at room temperature for 3 hours. After addition of methanol (8 ml) to the reaction mixture, poly-tert-butyl acrylate could be isolated as a white solid (635 mg). $M_n$=3,000 g/mol, $M_w/M_n$=1.69.

We claim:
1. A binuclear metal hydride complex of the formula (I)

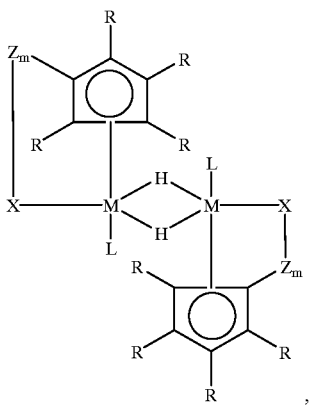

(I)

where the substituents and indices have the following meanings:

M is yttrium,

R is hydrogen, halogen, $C_1$–$C_{20}$-alkyl, $C_3$–$C_{10}$-cycloalkyl, $C_6$–$C_{15}$-aryl or $C_3$–$C_{30}$-organosilyl, where two adjacent radicals R can also form a saturated or unsaturated, cyclic or heterocyclic group having from 4 to 18 carbon atoms, Z is —SiR'$_2$—, —CR'$_2$—, GeR'$_2$—, BR'— or —O—, R' is $C_1$–$C_{20}$-alkyl, $C_3$–$C_{10}$-cycloalkyl, $C_6$–C15-aryl or alkylaryl having from 1 to 10 carbon atoms in the alkyl part and from 6 to 10 carbon atoms in the aryl part, m is 1 or 2, X is —O—, —S—, NR"—, —PR"—, —OR", —SR", —NR"$_2$ or —PR"$_2$, R" is hydrogen, $C_1$–$C_{20}$-alkyl, $C_3$–$C_{10}$-cycloalkyl, $C_6$–$C_{15}$-aryl, alkylaryl having from 1 to 10 carbon atoms in the alkyl part and from 6 to 10 carbon atoms in the aryl part or $C_3$–$C_{30}$-organosilyl and L is a low molecular weight, Lewis-basic, organic compound.

2. A binuclear metal hydride complex as claimed in claim 1, where in

M is yttrium,

R is $C_1$–$C_{10}$-alkyl or $C_3$–$C_{21}$-organosilyl, where two adjacent radicals R can also form a fused aromatic ring, Z is —SiR'$_2$' or —CR'$_2$—, R' is $C_1$–$C_{10}$-alkyl or $C_6$–$C_{10}$-aryl, m is 1, X is —NR"— or —PR"—, R" is $C_1$–$C_{10}$-alkyl, $C_6$–$C_{10}$-aryl or alkylaryl having from 1 to 6 carbon atoms in the alkyl part and from 6 to 10 carbon atoms in the aryl part and L is tetrahydrofuran, 2,5-dialkyltetrahydrofuran, dioxane, dialkyl ether, acetonitrile, triarylphosphine or halogenated triarylphosphine.

* * * * *

UNITED STATES PATENT AND TRADEMARK OFFICE
CERTIFICATE OF CORRECTION

PATENT NO. : 6,291,655 B1
DATED : September 18, 2001
INVENTOR(S) : Okuda et al.

It is certified that error appears in the above-identified patent and that said Letters Patent is hereby corrected as shown below:

Title page,
Item [57], ABSTRACT,
Line 3, after formula (I), "$C_3$-$C_1$-cycloalkyl" should be -- $C_3$-$C_{10}$-cycloalkyl --.

Column 10, claim 1,
Line 1, "$C_6$-C15-aryl" should be -- $C_6$-$C_{15}$-aryl --.

Column 10, claim 2,
Line 15, "where in" should be -- wherein --.

Signed and Sealed this

Twenty-sixth Day of February, 2002

Attest:

JAMES E. ROGAN
Attesting Officer     Director of the United States Patent and Trademark Office